United States Patent
Taylor et al.

[11] Patent Number: 5,183,702
[45] Date of Patent: Feb. 2, 1993

[54] BARRIER FABRICS

[75] Inventors: Jeffrey L. Taylor, Cincinnati, Ohio; Roy Luckenbach, Charlotte, N.C.; Michael Coco, Bridgeport; Carl Twickler, Easton, both of Conn.

[73] Assignee: Dover Corporation, New York, N.Y.

[21] Appl. No.: 679,735

[22] Filed: Apr. 3, 1991

[51] Int. Cl.⁵ .............................................. B32B 7/00
[52] U.S. Cl. ................................... 428/266; 428/241; 428/257; 428/258; 428/405; 428/446; 428/447; 128/849
[58] Field of Search ............... 428/266, 446, 257, 258, 428/447, 405, 95, 99, 198, 241

[56] References Cited

U.S. PATENT DOCUMENTS

| | | | |
|---|---|---|---|
| 4,303,712 | 12/1981 | Woodroof | 428/58 |
| 4,333,976 | 6/1982 | Okamoto et al. | 428/266 |
| 4,719,142 | 1/1988 | Modu | 428/266 |
| 4,994,317 | 2/1991 | Dugan et al. | 428/266 |

*Primary Examiner*—James J. Bell
*Attorney, Agent, or Firm*—Kinney and Schenk

[57] ABSTRACT

A liquid impermeable barrier fabric which resists penetration of liquids under finite hydraulic heads and maintains that capable after upwards of 75 institutional washing/sterilization cycles. The barrier fabric istructurally characterized by a silicone membrane attached to a fabric substrate. The substrate is a tightly woven fabric which is constructed of polyester yarns. Attachment of the membrane to the fabric substrate by a bonding mechanism in which the silicone material is in intimate contact with a substantial portion of the looped portions of the yarn, which define the surface of the fabric. This bonding mechanism also includes hydrophilicity of the yarn surfaces with which the silicone is in intimate contact. The fabric is treated with a hydrophilic finish to provide this aspect of the bonding mechanism. This barrier fabric is provided through the use of coating/-calendaring apparatus. A film of highly viscous, uncured silicone is formed with a Mooney viscosity of 45 and then pressed between rollers, into a fabric web, to attain the referenced intimate contact. The silicone is then cured.

9 Claims, 1 Drawing Sheet

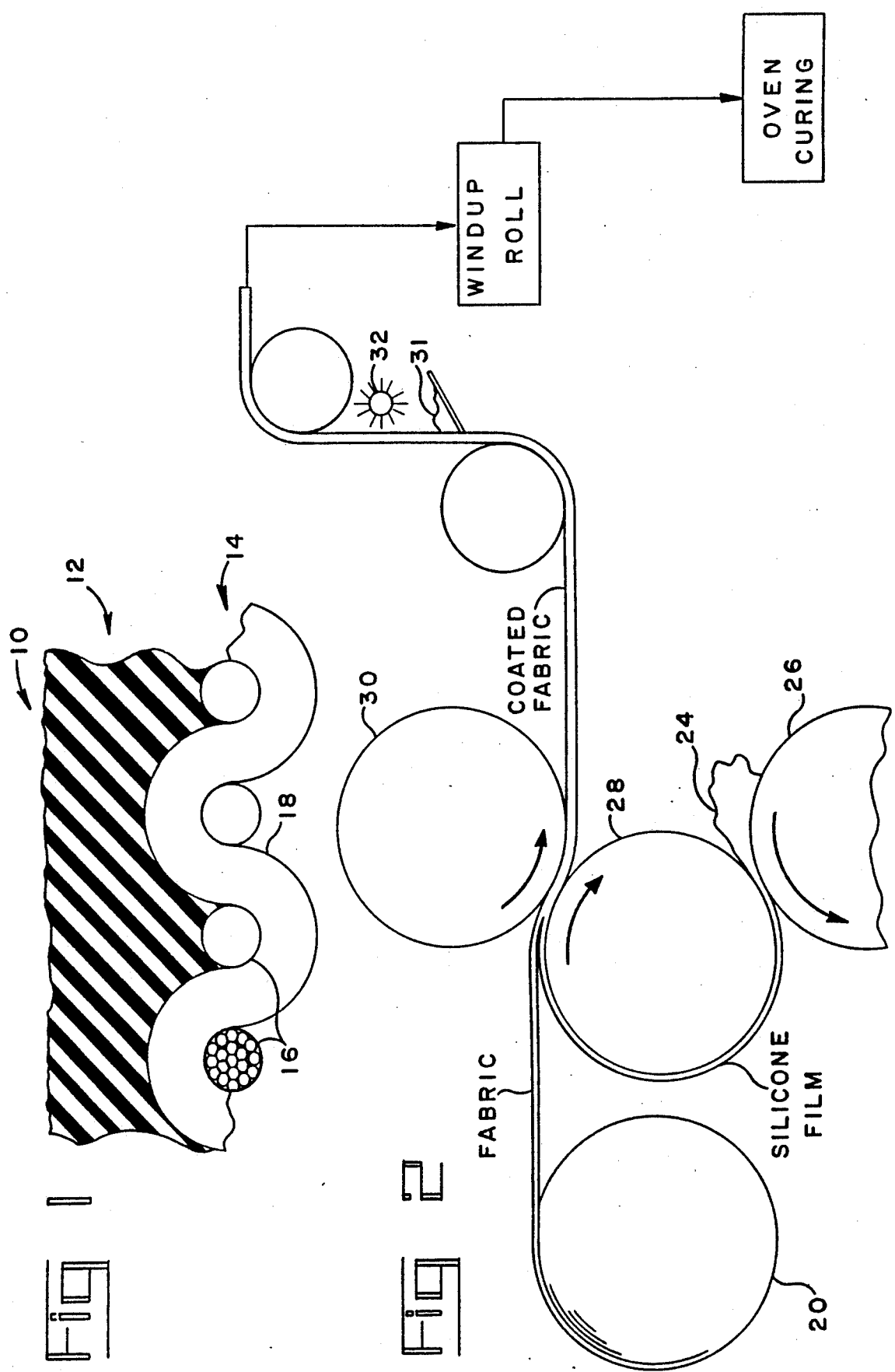

BARRIER FABRICS

The present invention relates to improvements in barrier fabrics and more particularly to an improved barrier fabric adapted for incorporation in reusable medical/surgical products, and also to improvements in the methods of making same.

Barrier fabrics are generically characterized by being impervious to penetration by liquids. There is a class of barrier fabrics which, additionally, are vapor permeable to provide what is termed breathability. Breathable barrier fabrics, for example, find widespread use in fabricating foul weather garments to provide protection against rain, while permitting the dissipation of perspiration. Breathable barrier fabrics are also used in constructing surgical drapes to protect a surgeon from blood and other fluids incident to a surgical procedure.

The point being made is that liquid impermeability is relative, being measured by the hydraulic head of liquid which can be resisted before the liquid penetrates the fabric. Generally speaking, liquid impermeability is inversely proportional to breathability, or the degree to which a fabric is permeable to vapor.

The present invention is directed to barrier fabrics which provide liquid impermeability, without regard to any breathability function.

More specifically, the present invention is directed to barrier fabrics adapted for incorporated in reusable, medical/surgical products.

In one specific aspect, the invention is directed to fabrics which are specifically adapted to be used in constructing surgical gowns, to provide the highest degree of possible protection from such potentially fatal microorganisms as the AIDS virus. Breathable barrier fabrics have been previously used for this purpose, in surgical gowns, to avoid discomfort for the surgeon during an extended surgical procedure. While these barrier fabrics do provide a high degree of reliability in preventing strike through of blood and the like, there is now a demand for a higher degree of protection, i.e., liquid impermeability, at the sacrifice of the breathability feature.

Reusable, surgical gowns, surgical drapes and other reusable medical/surgical products have further requirements, which distinguish them from other products, or garments that incorporate barrier fabrics. This is to say that, after each use, a reusable surgical gown, must be washed, dried and sterilized for subsequent reuse. These procedures involve harsh detergents and high temperatures which can quickly degrade the gown and limit the number of times the gown can be reused.

A typical, institutional washing/sterilization cycle for such reusable medical/surgical products generally comprises an initial flush in which the products are soaked in water at 90°-100° F. for three to five minutes. The products are then soaked in an alkali (with a ph in excess of 10) bath at 120°-140° F. for three to five minutes to loosen dirt. Next the products are placed in a detergent bath at approximately 160° F. for approximately eight to ten minutes. Next is a bleach bath at approximately 160° F. for approximately five minutes. This is followed by one or more rinsings at temperatures which may be progressively reduced from 140° to ambient temperature. Finally, there is a acid sour bath in which the ph is adjusted to the four to five range, and in which a softening agent may also be employed. There is then one or more, rinse baths.

The products are mechanically agitated in some, if not all of these baths. Also, following each bath, there is an extraction (spin) cycle to minimize the liquid carried over to the succeeding process.

The products are then dried in a tumbling dryer at an average temperature of 160° F. Typical drying times for products are in the order of 20 to 40 minutes. It is to be noted that there can be hot spots in such dryers, which can subject the products to temperatures in excess of 400° F.

After drying, the products are placed in an autoclave and sterilized by pressurized steam at a temperature of approximately 270° F., for ar least four minutes.

These harsh conditions are several orders of magnitude greater that those existing in the laundering, or dry cleaning of barrier fabrics incorporated in ordinary garments. In fact, many of the barrier fabrics, intended for use in normal garments, such as foul weather gear, become unusable after a single, or relatively few, institutional washing/sterilization cycles.

It is also readily apparent that acquisition costs and the number of times a surgical gown can be reused, have a direct bearing on the per use cost of a surgical gown. It will also be noted that there are disposable surgical gowns and other medical/surgical products in the market. The per use cost of such disposable items is, in essence, simply their acquisition cost and cost of disposal. Disposable gowns have an advantage in convenience. Reusable gowns have an advantage in that they have a drapability and feel, which is preferred over that of disposable gowns, which are fabricated of nonwoven fabrics. Drapability and feel are factors of the "hand" of the textile fabrics employed in constructing reusable surgical gowns.

All of this is to emphasize that there is a competitive motivation to minimize the per use cost of reusable surgical gowns and other reusable, medical/surgical garments and products.

Barrier fabrics represent a highly developed and crowded art, as is apparent from the extremely large number of patents disclosing the proposed use of a wide variety of constructions and constituents to provide the barrier function, many of which have had some measure of commercial acceptance.

However, none of these prior barrier fabrics fully meet the ends sought herein, namely the provision of highly effective liquid barrier which survives repeated institutional washing/sterilization cycles and, further, has a "hand" which approximates, or at least approaches the "hand" of textile fabrics.

Accordingly, the object of the present invention is to provide a barrier fabric which overcomes the shortcomings of prior art fabrics employed in the construction of reusable medical/surgical products, to the end that the per use cost of such products will be minimized and made more competitive with, or provide a competitive cost advantage over corresponding disposable, medical/surgical products.

The ends of the invention, in accordance with its broad aspects may be attained by a barrier fabric for use in reusable medical/surgical products, which are to be washed, dried and sterilized subsequent to each use. This barrier fabric is functionally characterized in that it is impermeable to liquids under a pressure no less than five pounds per square inch. It is further characterized in that this impermeability standard is maintained after the barrier fabric has been subject to at least 75 institutional washing/sterilization cycles.

This barrier fabric comprises a liquid impervious membrane and a fabric substrate to which the membrane is attached and is characterized in that the membrane is formed by a typical, methyl vinyl silicone polymer. The fabric substrate is characterized in being formed of tightly woven polyester yarns, which form a plurality of curved yarn portions in the form of "nubs" which define one surface of the fabric. The silicone membrane is attached to this surface of the fabric substrate by a bonding mechanism comprised of portions of the membrane conforming to and in intimate contact with a substantial portion of each of said "nubs", and a hydrophilic surface characteristic of the portions said said "nubs", with which the membrane is in intimate contact.

Further features of the invention include the average thickness of the silicone membrane being between approximately 0.002 inches and 0.010 inches and more preferable 0.003 inch. The silicone membrane has a hardness between approximately 30 and 70 and preferably 50 as measured on the Shore "A" scale.

The fabric substrate is, preferably, a plain woven fabric having a porosity of less than ten cubic feet per minute per square yard, as measured by the Frazier Test.

The fabric substrate may also be characterized as, preferably being a plain woven fabric, which has a griege weight of approximately 2.3 ounces per square yard, with the warp yarns and filling yarns have a denier of approximately 70, and constructed with approximately 138 ends per inch and approximately 86 picks per inch. Additional advantages are found where the warp yarns are 70/34 false twist, set yarn and the filling yarns are 70/68 untexturized yarn.

A further feature of the invention is found the outer surface of the membrane being textured by the application of talc thereto, prior to curing of the silicone membrane.

The method aspects of the invention may be practiced with existing calendaring/coating apparatus wherein a film of highly viscous, uncured silicone is coated onto a web of fabric. Features of the invention, particularly unique to its method aspects include providing a film of uncured silicone with a Mooney viscosity ranging between 30 and 60 and preferably approximately 45. Additionally, talc may be applied to the silicone film, after it has been attached to the fabric web and prior to curing of the silicone.

The above and other object and features of the invention will be apparent from the following description of the fabric of the present invention, wherein specific exemplification of the improved fabric is set forth, with reference to the accompany drawings and the novelty thereof pointed out in the appended claims.

IN THE DRAWING

FIG. 1 is a cross section, on a highly enlarged scale, of the barrier fabric of the present invention; and FIG. 2 is a diagrammatic illustration of the process for producing the fabric of FIG. 1.

The fabric of the present is generally indicated by reference character 10 in FIG. 1 and comprises a silicone membrane 12 and a fabric substrate 14.

The substrate 14 is a highly bulked, tightly woven fabric, preferably plain woven (one by one) comprised of warp yarns 16 and filling yarns 18.

Both the warp yarns and filling yarns are continuous, multifilament, polyester yarns, which are readily available from various commercial sources.

The substrate fabric is further characterized in that it has 138 ends per inch and 86 picks per inch, employing 70/34, false twist, texturized, set polyester, warp yarns and 70/68 untexturized, i.e., fully oriented, polyester filling yarns.

The fabric substrate is also characterized by a griege weight of approximately 2.26 ounces per square yard. In the usual case the fabric will be dyed and a hydrophilic finish is applied, to the end that the hydrophobic surfaces of the polyester yarn filaments are hydrophilic. The dried and hydrophilic finished fabric has a weight of approximately 2.6 ounces per square yard.

The membrane 12 is a cured, silicone polymer having an average thickness in the order of 0.003 inch. The silicone polymer may be what is known as a typical, methyl vinyl silicone. The silicone material is modified, pursuant to procedures known in the art, through the addition of silica fillers, to have a durometer, or hardness, of approximately 50 on the Shore "A" scale.

Silicone has been selected as the membrane polymer because, among other reasons, it is, essentially, chemically resistant to degradation by the alkalis and acids and detergents involved in institutional washing, as well as the elevated temperatures involved, all as has been set forth above. Thus the selected membrane material is not subject to degradation when incorporated in reusable, medical/surgical products.

The hardness parameter of the silicone membrane has been found critical to achieving characteristics necessary to attain the ends of the present invention. These factors include attaining the desired liquid impermeabilty while at the same time providing a barrier fabric which has a "hand" which approximates that of plain textile fabrics.

As will later, more fully appear in the description of the method employed in forming this fabric, the membrane 12 is attached to the fabric substrate 14 by an enhanced, and highly effective bond, which is attained by the application of a hydrophilic finish to the fabric substrate 14, prior to application of the membrane 12 thereto.

Polyester, as an inherent characteristic, is hydrophobic. In many fabric products, it is desired that the fabric possess hydrophilicity. This need has been met by the development of hydrophilic finishes, or treatments, which provide a hydrophilic characteristic to the polyester surfaces of the filaments comprised in the yarns employed in constructing the fabric. The treated fabric then possesses water absorbent properties not found in untreated polyester fabrics.

Returning to the fabric substrate 12, it will be seen that the woven warp and filling yarns comprise curved portions. These curved portions form a plurality of closely spaced, projecting "nubs" which define the surfaces of the fabric. The bonding mechanism, whereby the membrane is attached to the fabric is in part derived from an intimate contact between these curved portions, or "nubs". This is to say that there is intimate contact between the looped portions of the yarns and not merely contact with the tops of the "nubs". This bonding mechanism is also derived from the hydrophilic finish treatment of the polyester yarns, which provides the surfaces of their filaments with hydrophilicity.

As has been previously indicated, the fabric substrate is tightly woven, and has been characterized above in terms of ends and picks and yarn deniers. These parameters define a fabric which has minimum sized interstices between the yarns and their filaments. Minimum interstice size may also be defined by the porosity of a fabric. It has been found that the fabric substrate 12 should have a porosity which limits air flow to less than 10 cubic feet per minute per square yard, as measured by the Frazier Test (ASTM-737-75).

By obtaining intimate contact between the "nubs" which define the surface of a fabric having a minimum interstice size, characterized above, it has been found that a higher degree of reliability is attained in providing a the liquid impermeability function, with a minimum thickness membrane.

The "nubbed" character of the surface of a woven fabric also explains the earlier reference to the thickness of the surface be expressed as an "average" to take into account the fact that the thickness will be less where the membrane overlies the top of a "nub".

It should be further appreciated that the small interstice sizes of the fabric permits a reasonable tolerance in preventing a breakdown in impermeability, i.e., strike-through, where the membrane thickness is less than the desired 0.003 inch.

The process for manufacturing the barrier fabric 10 is diagrammatically illustrated in FIG. 2.

A web of fabric substrate 14 is drawn from a supply roll 20 and fed to calendaring/coating apparatus 22, which coats the membrane 12 to one surface of the substrate. The fabric substrate is a tightly woven fabric, as above defined and characterized. This fabric has, further been treated with a hydrophilic finish.

The calendaring/coating apparatus may be of any well know design, and, in FIG. 2, is abbreviated to illustrate its basic functions of forming a highly viscous, or semi-liquid polymer film and then applying that film to a fabric substrate.

Thus, there is a batch source, or supply, of uncured silicone, indicated by reference character 24, which has been pre-mixed with a polymerization agent. As previously indicated, this would be an uncured, typical, methyl vinyl silicone, an exemplary silicone being from Dow Corning, Inc. Midland Michigan, under the designation "Silastic".

This uncured silicone is modified by the addition of silica filler, so that, in its cured state, it has a hardness of approximately 50 on the Shore "A" scale.

The uncured silicone polymer can be appropriately modified, by conventional means, to provide, within a relatively large, range, a desired viscosity. For purposes of the present invention, it has been found that the viscosity of the uncured silicone resin should have a Mooney Viscosity rating of 45, at room temperature. This viscosity contributes to obtaining the desired intimate contact between the silicone material and the fabric "nubs", discussed above.

The source batch (24) is spread and squeezed between calendaring rolls 26, 28 to form a thin film of uncured silicone, which is carried on the surface of roll 28. The thickness of this film approximates the average thickness of the membrane 14 in the end product.

The web of textile fabric substrate is fed, in overlying relation onto the film of uncured silicone and pressed thereagainst by a pressure roll 30.

The fabricate substrate is thus coated with the uncured, silicone polymer. The viscous state of the uncured silicone, permits it to be forced into the intimate contact with the yarns of the fabric 14. This intimate contact is illustrated in FIG. 1.

The coated fabric is then fed to a vertically upward run. Talc is applied, at 30, to the exposed surface of the uncured silicone membrane. Excess talc is then removed by a brush 32. The coated fabric is then wound into roll form in order that it may be later fed through an oven to heat cure the silicone membrane.

The coated fabric is then fed through an oven to heat cure the silicone membrane. Conventional temperatures and oven dwell times can be employed in heat curing the silicone membrane.

The talc coating was originally provided to serve as a parting agent so that the uncured resin could be rolled on itself and later unrolled and fed through the curing oven.

It has been discovered that the talc coated silicone, when cured, has a roughened surface. Also, a small amount of talc remains in the surface of the silicone, after curing. This residual talc, and the roughened surface, contribute to the improved "hand" of the barrier fabric 10.

It will be further noted that polymer membranes of prior barrier materials have been vulnerable to degradation by abrasion. When used in surgical/medical products, barrier fabrics are subject to substantial abrasion. They are further subject to abrasion in the institutional washing process. Thus it has been a conventional practice to protect such membranes from abrasion by attaching protective substrates to opposite sides of the membrane.

The silicone membrane of the present invention is less subject to abrasion than most barrier fabrics that have been used in reusable, surgical/medical products. In part, it is believed that this abrasion resistance improvement may be attributed to the talc treatment of the uncured silicon membrane. In any event, it is not necessary for the outer surface of the membrane 12 to be protected by a fabric layer attached thereto, as is the case of a laminated barrier fabric. It is however, preferably that the membrane be protected by a fabric shield. This end may be attained providing a barrier fabric piece of a desired outline and then securing a light weight fabric piece, or shield, of corresponding outline in overlying relation to the exposed membrane surface, by peripheral stitching. Alternatively, the barrier fabric 10 may be incorporated into a medical/product in such a fashion that it is secured to another fabric piece of the product so that that other fabric piece serves as a protective shield.

At this point, it will be acknowledged that the coating of silicone membranes is known. The present invention differs from those known processes in that the barrier fabric produced, as taught herein, fulfills the needs of reusable, medical/surgical products in a fashion far superior to the silicone coated products hitherto produced.

The attainment of these ends lies in the several features described, including the silicone polymer, its viscosity in an uncured state at the time of being calendared onto the fabric substrate, the hydrophilic finish, modification of the fabric, the weight of the fabric substrate, the thickness of the silicone membrane, the durometer, or hardness of the cured silicone membrane, as well as the fabric yarns and the porosity of the fabric, which is minimized by the tightly woven construction employed, as related to yarn deniers and pick and end counts and/or porosity.

Barrier fabric manufactured pursuant to the foregoing teachings is not only liquid impermeable, but resists penetration by liquids under substantial hydraulic heads. Liquid pressures on medical/surgical products, such as gowns and drapes, are nominal. This is to say that, in the usual case, blood splashed on a gown has no hydraulic head tending to cause it to penetrate, or strike through, the gown. Likewise in further exemplification of this point, in the case of a surgical drape, a saline solution might flow onto the drape, but would have only a nominal hydraulic head tending to cause a strikethrough. Nonetheless, there can be occasions, such as where a surgeon wipes a blood covered scalpel against the barrier fabric, where there will be finite hydraulic pressures which could cause a strikethrough.

It has been found that reliable protection against strikethroughs can be obtained where the liquid impermeability of the barrier fabric resists penetration of liquid under a pressure of at least five pounds per square inch. Barrier fabrics manufactured pursuant to foregoing teachings provide this minimum impermeability standard, and, in fact, are resistant to penetration of liquids under hydraulic heads substantially in excess of five pounds per square inch.

The significant characteristic of the present barrier fabric is that this minimum impermeability requirement is met by the barrier fabric after it has been processed for subsequent reuse by the institutional washing/sterilization cycle specified above. While the parameters of that cycle are not governed by any fixed standard, the cycle itself is understood by those skilled in the art. An deviations from the description of that cycle, herein set forth, would involve only a matter of relatively small degree, insofar as the harshness of the conditions which tend to degrade the barrier fabric is concerned. This is to say that the term "institutional washing/sterilization cycle", as herein used is a meaningful term to those skilled in the art and a proper standard for measuring the functional characteristics of barrier fabrics.

The barrier fabric of the present invention is unique in that following a minimum of 75 institutional washing/sterilization cycles, the barrier fabric still meets the minimum impermeability requirement of resisting penetration of liquids under a hydraulic head of about five pounds per square inch. In fact, this minimum standard is maintained after the fabric has been processed by institutional washing/sterilization cycles in excess of 100.

The present barrier fabric is thus, highly durable. It is significant to note that following 75, or more, institutional washing/sterilization cycles, that there is little, or no, visible delamination of the fabric substrate 14 from the membrane 12.

While there are preferred parameters, as indicated above, improved fabric characteristics can be obtained within relatively narrow ranges. Thus, for example, the viscosity of the uncured silicone can range between a Mooney viscosity rating of 30-60 and the cured durometer may range between 30 and 70 on the Shore A scale.

It will also be appreciated that there will be some measure of deviation from preferred parameters defining the fabric substrate 14. Thus, there are alternate yarn deniers and pick and end counts, and resultant fabric weights, which would provide an equivalent, highly bulked, tightly woven, low porosity fabric.

The preferred, hydrophilic finish is generically characterized as involving a method of contacting a textile with a swelling agent and a base and heating to alter the textile, and then acidifying the treating bath and contacting the textile with a hydrophilic polymer, all of which is more fully taught in U.S. Pat. No. 4,803,256. One advantage of this hydrophilic finish treatment is that the resultant hydrophilicity of the treated fabric is permanent. Chemicals for this treatment are available from Dow Corning, Inc. Midland, Mich. under the trademark Vestar. Other hydrophilic finishes, which do not have this permanent characteristic, may also be employed. Exemplary of such hydrophilic finishes are Milesase T available from ICI America, Inc., Wilmington, Del., Alkaril QFC available from Chemical, Inc., Winds, Ga. and Scotchgaurd Stain Release Fabric Treatment FC-22, available from the 3M Company, St. Paul, Minn.

Having thus described the invention, what is claimed as novel and desired to be secured by Letters Patent of the United States is:

1. A barrier fabric for use in reusable medical/surgical products, which are to be washed, dried and sterilized subsequent to each use,
    said barrier fabric being functionally characterized in that it is impermeable to liquids under a pressure no less than five pounds per square inch, and
    this impermeability standard is maintained after the barrier fabric has been subject to at least 75 institutional washing/sterilization cycles,
    said barrier fabric comprising
    a liquid impervious membrane and
    a fabric substrate to which the membrane is attached, characterized in that
    the membrane is formed by a typical, cured methyl vinyl silicone polymer,
    the fabric substrate is formed of tightly woven polyester yarns, which form a plurality of curved yarn portions in the form of "nubs" which define one surface of the fabric, and
    the silicone membrane is attached to said one surface of the fabric substrate by a bonding mechanism comprised of
        portions of the membrane conforming to and in intimate contact with a substantial portion of each of said "nubs", and
        a hydrophilic surface characteristic of the portions of said "nubs", with which the membrane is in intimate contact.

2. A barrier fabric as in claim 1 further characterized in that
    the average thickness of the silicone membrane is between approximately 0.002 inches and 0.010 inches.

3. A barrier fabric as in claim 2 further characterized in that
    the silicone membrane has a hardness between approximately 30 and 70 as measured on the Shore "A" scale.

4. A barrier fabric as in claim 2 further characterized in that
    the fabric substrate is a plain woven fabric has
    a griege weight of approximately 2.3 ounces per square yard
    the warp yarns and filling yarns have a denier of approximately 70, and
    is constructed with approximately 138 ends per inch and approximately 86 picks per inch.

5. A barrier fabric as in claim 4 further characterized in that
   the warp yarns are 70/34 false twist, set yarn and
   the filling yarns are 70/68 untexturized yarn.

6. A barrier fabric as in claim 5 further characterized in that
   the fabric substrate has been dyed and a hydrophilic finish applied thereto in order to provide the hydrophilic surface characteristic, and
   the finished weight of the fabric substrate is approximately 2.6 ounces per square yard, and
   the silicone membrane has
   a thickness of approximately 0.003 inch and
   the hardness of the membrane is approximately 50 as measured on the Shore "A" scale.

7. A barrier fabric as in claim 1 further characterized in that
   the outer surface of the membrane is textured by the application of talc thereto, prior to curing of the silicone membrane.

8. A barrier fabric as in claim 6 further characterized in that
   the outer surface of the membrane is textured by the application of talc thereto, prior to curing of the silicone membrane.

9. A barrier fabric as in claim 2 further characterized in that
   the fabric substrate is a plain woven fabric having a porosity of less than ten cubic feet per minute per square yard, as measured by the Frazier Test.

* * * * *

UNITED STATES PATENT AND TRADEMARK OFFICE
CERTIFICATE OF CORRECTION

PATENT NO. : 5,183,702
DATED : Feb. 2, 1993
INVENTOR(S) : Jeffery L. Taylor et al.

It is certified that error appears in the above-indentified patent and that said Letters Patent is hereby corrected as shown below:

Title page, delete item [73] Assignee : Dover Corporation, New York, N.Y." And insert Standard Textile Company, Inc. Cincinnati, Ohio and Fairprene Indstrial Products, Inc., Fairfiled, Conn.

Signed and Sealed this

Fourth Day of July, 1995

Attest:

BRUCE LEHMAN

Attesting Officer

Commissioner of Patents and Trademarks